(12) United States Patent
Konawa

(10) Patent No.: US 11,173,075 B2
(45) Date of Patent: Nov. 16, 2021

(54) ABSORBENT ARTICLE

(71) Applicant: DAIO PAPER CORPORATION, Ehime (JP)

(72) Inventor: Satoko Konawa, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 530 days.

(21) Appl. No.: 16/307,704

(22) PCT Filed: Jun. 8, 2017

(86) PCT No.: PCT/JP2017/021266
§ 371 (c)(1),
(2) Date: Dec. 6, 2018

(87) PCT Pub. No.: WO2017/213211
PCT Pub. Date: Dec. 14, 2017

(65) Prior Publication Data
US 2019/0262193 A1 Aug. 29, 2019

(30) Foreign Application Priority Data
Jun. 9, 2016 (JP) .............................. JP2016-114960

(51) Int. Cl.
*A61F 13/47* (2006.01)
*A61F 13/472* (2006.01)
(Continued)

(52) U.S. Cl.
CPC ........ *A61F 13/47236* (2013.01); *A61F 13/47* (2013.01); *A61F 13/51108* (2013.01);
(Continued)

(58) Field of Classification Search
CPC ................ A61F 13/4704; A61F 13/472; A61F 13/47236; A61F 13/4756; A61F 13/51108; A61F 13/533; A61F 13/534; A61F 13/536
See application file for complete search history.

(56) References Cited

U.S. PATENT DOCUMENTS

| 8,481,806 B2 * | 7/2013 | Ueminami | A61F 13/4702 |
| | | | 604/380 |
| 8,715,258 B2 * | 5/2014 | Munakata | A61F 13/533 |
| | | | 604/385.101 |
| 2008/0281287 A1 * | 11/2008 | Marcelo | A61F 13/4756 |
| | | | 604/383 |

\* cited by examiner

*Primary Examiner* — Catharine L Anderson
(74) *Attorney, Agent, or Firm* — Wenderoth, Lind & Ponack, L.L.P.

(57) ABSTRACT

On a skin-contact surface on a front-surface side of a sanitary napkin 1, in a plan view, a concave low compression part 10 obtained by denting, from a skin-contact surface side, a closed region part partitioned by an inside curve 12 formed of a curved line swelling on a front end side of the sanitary napkin 1, and an outside curve 13 that is located on a front end side than the inside curve 12, is formed of a curved line swelling on a front end side of the sanitary napkin 1 and has both ends that are connected respectively to the both ends of the inside curve 12 is formed. In the low compression part 10, a plurality of high compression parts 11 formed discretely respectively along the inside curve 12 and outside curve 13 is formed. The high compression parts 14 formed along the inside curve 12 are arranged over an entire length of the inside curve 12, and the high compression parts 15 formed along the outside curve 13 are arranged on a center part of the outside curve 13, and the high compression parts are not arranged at both end parts of the (Continued)

outside curve 13. Sanitary napkin 1 makes it easy to deform along a shape of a body and make it difficult to generate twists or leakage.

8 Claims, 6 Drawing Sheets

(51) Int. Cl.
    *A61F 13/511*     (2006.01)
    *A61F 13/533*     (2006.01)
    *A61F 13/534*     (2006.01)
    *A61F 13/536*     (2006.01)

(52) U.S. Cl.
    CPC .......... *A61F 13/533* (2013.01); *A61F 13/472* (2013.01); *A61F 13/534* (2013.01); *A61F 13/536* (2013.01)

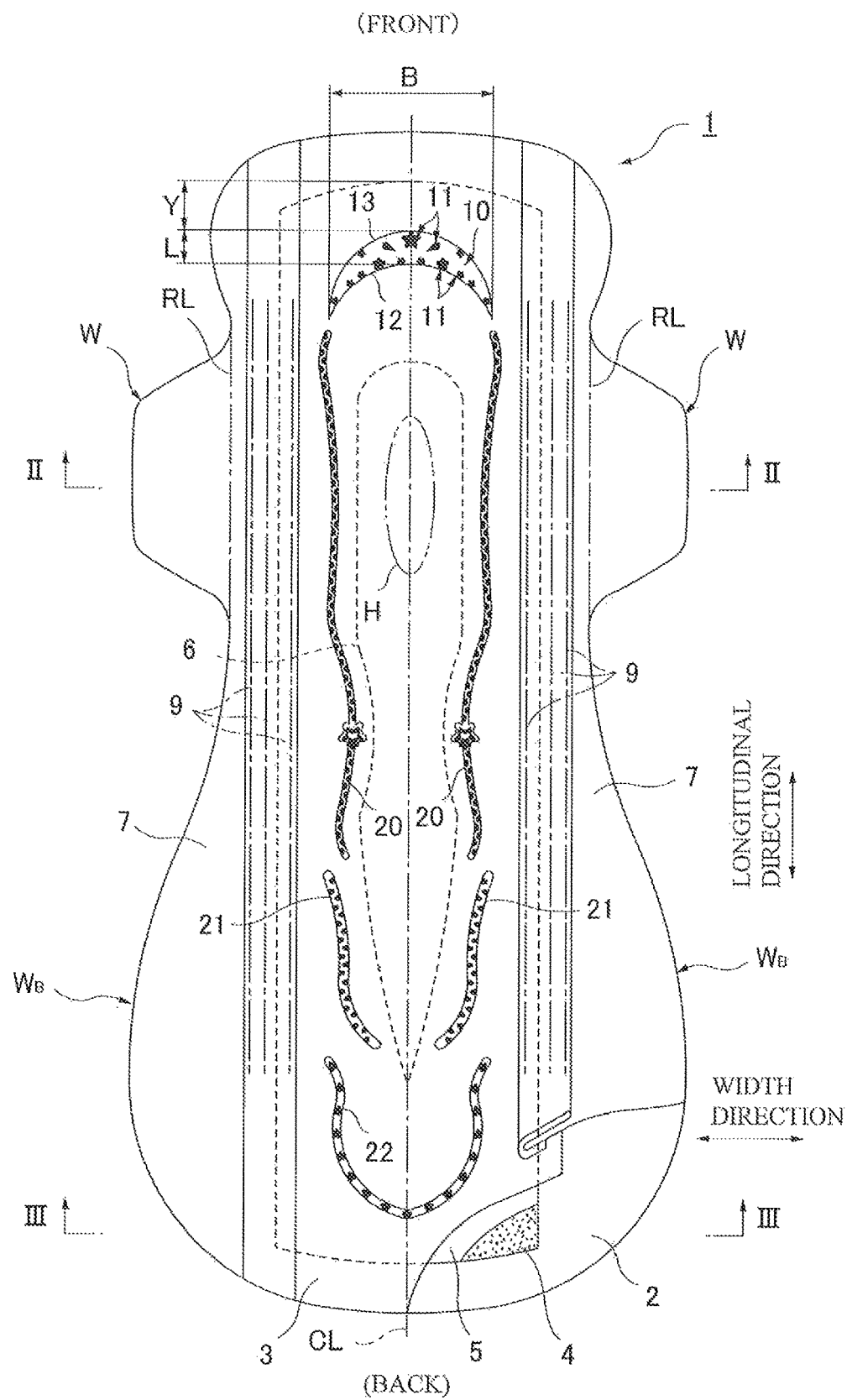
[Fig. 1]

[Fig. 2]
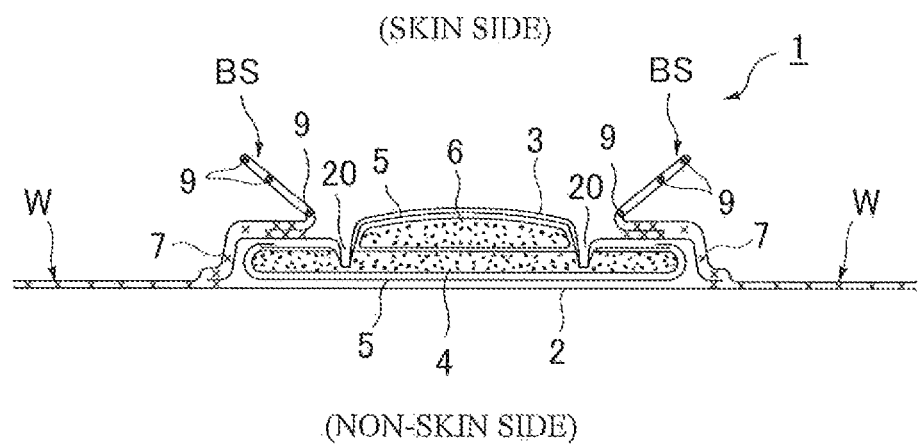
[Fig. 3]
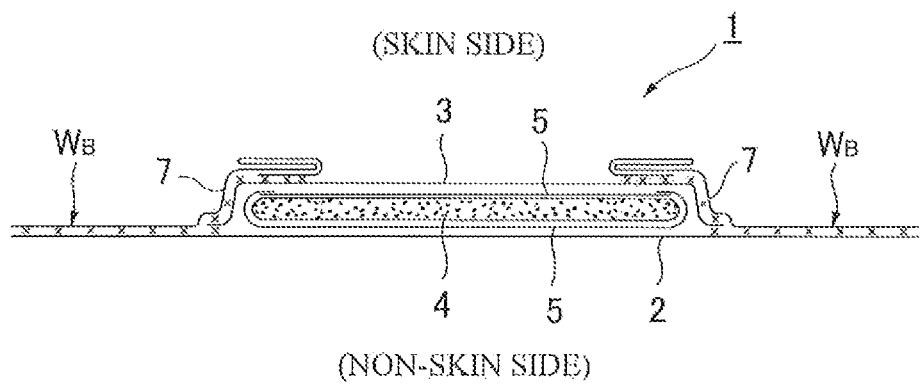

[Fig. 4]
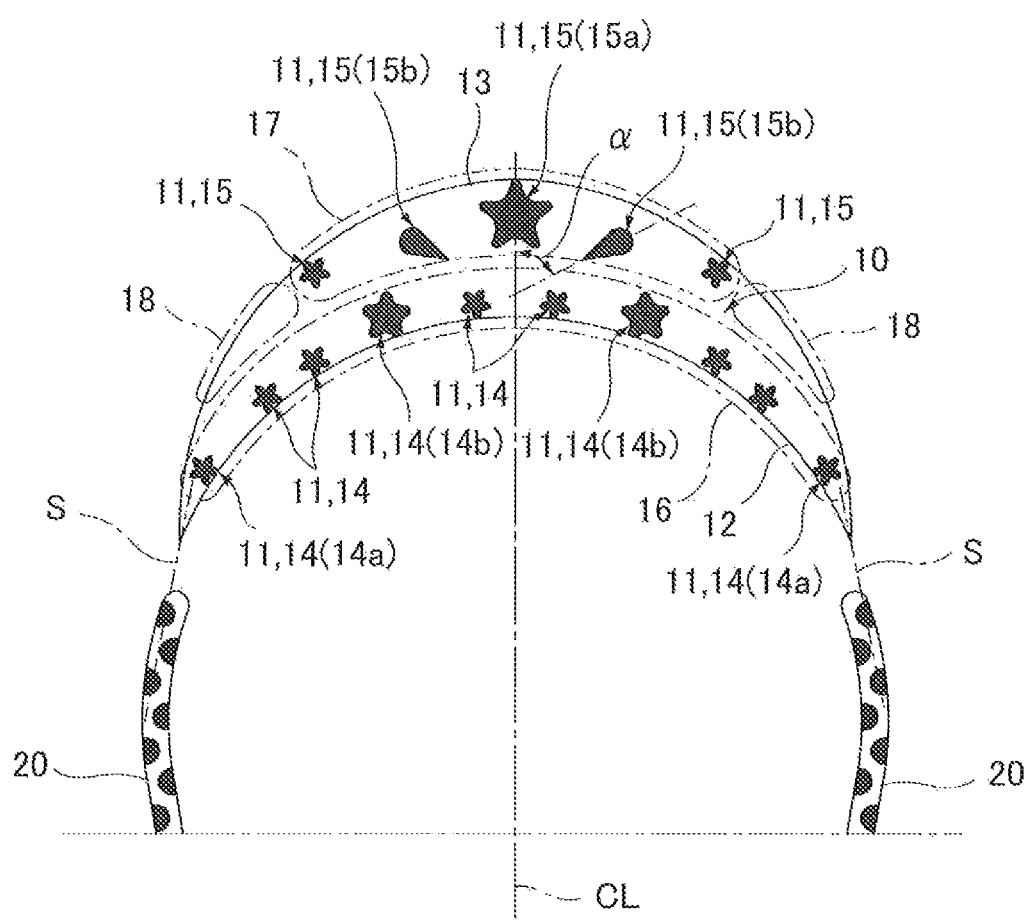

[Fig. 5]
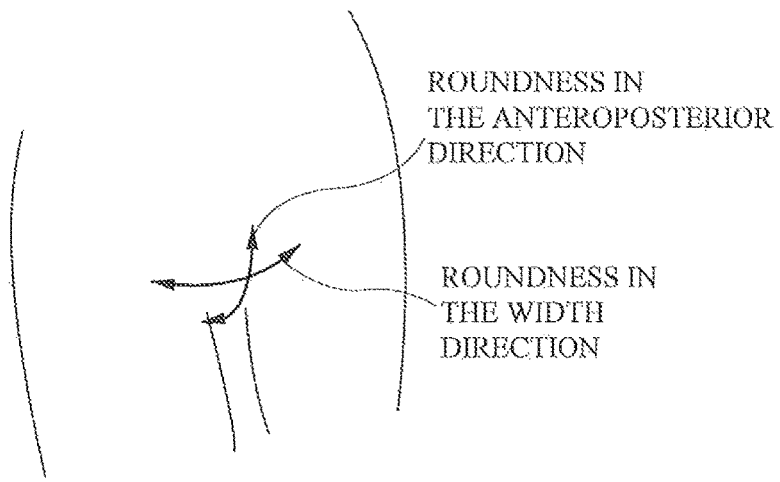
[Fig. 6]
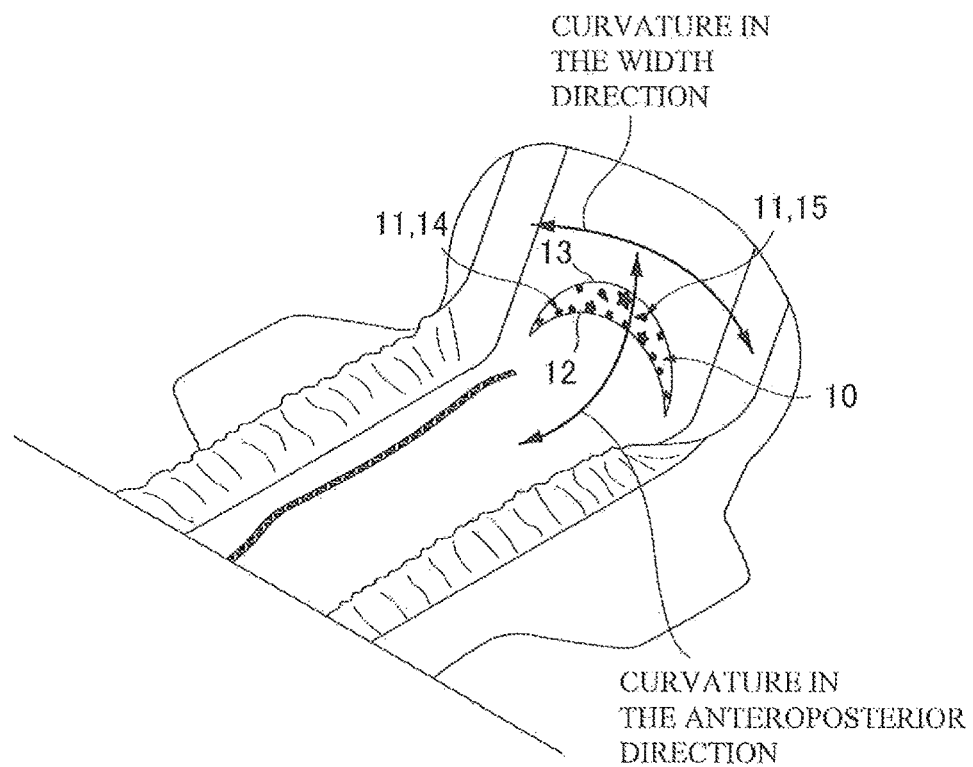

[Fig. 7]
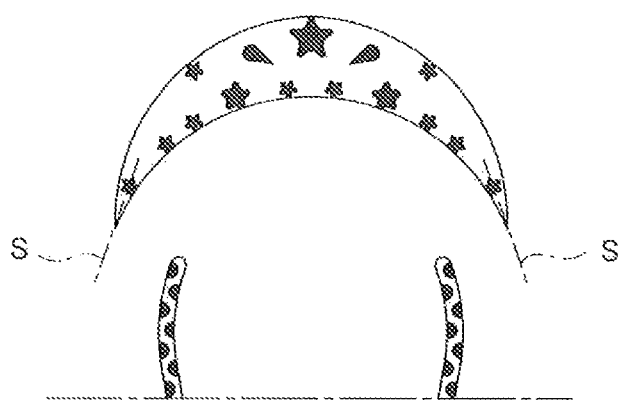

[Fig. 8]
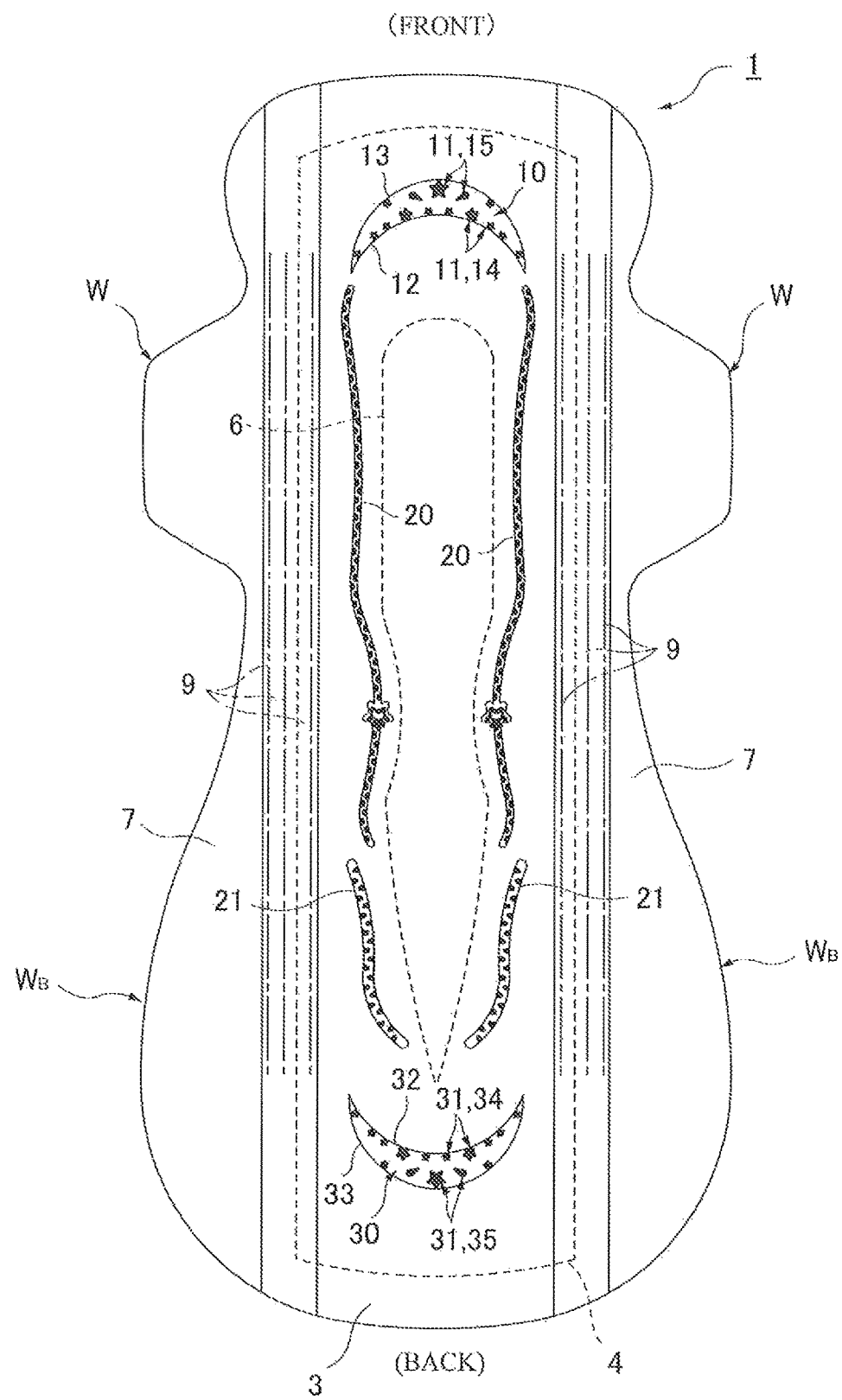

ABSORBENT ARTICLE

TECHNICAL FIELD

The present invention relates to an absorbent article that is used mainly in sanitary napkins, vaginal discharge sheets, incontinence pads, or toiletries, in more detail, to an absorbent article in which a substantially crescent shape compression part is formed by denting from a skin-contact surface side in a plan view.

BACKGROUND ART

So far, as absorbent articles such as pantiliners, sanitary napkins, and incontinence pads, ones in which an absorber made of cotton-like pulp or the like is interposed between an impermeable back-surface sheet such as a polyethylene sheet or a polyethylene sheet laminate nonwoven fabric and a permeable front sheet such as a nonwoven fabric or a permeable plastic sheet are known.

Since this kind of absorbent articles have experienced various improvements, in order to prevent leakage of body liquid and to make it easy for an absorbent article to deform along a shape of the body in wearing, there are technologies for forming the compression part dented from a skin-contact surface side to a non-contact skin side into various forms.

For example, in Patent Literature 1 below, a technology of forming a circular emboss groove toward a front side on a back side of an absorber is proposed. Furthermore, in Patent Literature 2 below, an absorbent article that includes a front compressed groove extending in the width direction in a front region and a pair of vertical compressed grooves extending in the longitudinal direction on both side parts along the longitudinal direction in a region facing an excretion part, wherein the front compressed grooves and each of the vertical compressed grooves are communicated while forming a bundling part bundled toward the inside in the width direction, and the front compressed grooves have a dented part dented toward aback side at a center part in the width direction is proposed.

PRIOR ART LITERATURES

Patent Literatures

Patent Literature 1: JP H11-113955 A
Patent Literature 2: JP 2015-97719 A

SUMMARY OF THE INVENTION

Problem to be Solved by the Invention

In one described in the Patent Literature 1, it is considered that by deforming the absorbent article in the longitudinal direction with the circular emboss groove as a base point, the absorbent article tends to follow roundness in an anteroposterior direction of a body. However, because there is no consideration of the deformation along the roundness in the width direction of the body, the fitting property to the body is insufficient and there was fear of generation of twists or leakage.

Furthermore, in the absorbent article described in the Patent Literature 2, a front compressed groove has a circular right convex compressed groove protruded in convex to a right diagonal front direction and a circular left convex compressed groove protruded in convex to a left diagonal front direction, wherein since the right convex compressed groove and left convex compressed groove intersect and are connected in conjunction at a dented part dented in a V-shape at a central line, when the central part bends in the width direction with the dented part as a base point, a wrinkle in the vertical direction tended to occur in the front part. Furthermore, since the circular convex compressed grooves protruded in convex in a diagonal front direction respectively in left and right are formed, it is considered that the rigidity of front both side parts is enhanced by the compressed groove and front both side parts become difficult to deform along the roundness in the width direction of the body. Therefore, there is a fear that a gap is generated between a skin surface and the absorbent article to result in causing twists or leakage.

There, a main problem of the present invention is to provide an absorbent article that makes it easy to deform along a shape of the body and makes it difficult to generate twists or leakage.

Means for Solving the Problem

As the present invention according to claim 1 for solving the problem, in an absorbent article in which an absorber is interposed between a permeable front-surface sheet and a non-permeable back-surface sheet, an absorbent article, wherein on a skin-contact surface on a front side of the absorbent article, in a plan view, a concave low compression part obtained by denting, from a skin-contact surface side, a closed region part partitioned by an inside curve formed of a curved line swelling on a front end side of the absorbent article, and an outside curve that is located on a front end side than the inside curve, formed of a curved line swelling on a front end side of the absorbent article, and has both ends that are respectively connected the both ends of the inside curve is formed; and, in the low compression part, a plurality of high compression parts is discretely formed respectively along the inside curve and outside curve, wherein the high compression parts formed along the inside curve are arranged over an entire length of the inside curve, and the high compression parts formed along the outside curve are arranged at a center part of the outside curve and are not arranged at both end parts of the outside curve is provided.

In the invention according to claim 1, since the inside curve is toughened over an entire length by the high compression part arranged over an entire length of the inside curve, and the central part of the outside curve is toughened by the high compression part arranged at the central part of the outside curve, the absorbent article tends to curve in the longitudinal direction with these toughened curved parts as a base point, and a front side rises up along the inside curve, thus, the absorbent article tends to deform along the roundness in the anteroposterior direction of the body. Furthermore, since the high compression part is not arranged to both end parts of the outside curve, the rigidity is degraded relative to a region where the high compression part is formed, therefore both side parts on a front side than the low compression part tends to curve on a skin side, thus, a front part of the absorbent article tends to deform along the roundness in the width direction of the body. Thus, since the front side of the absorbent article tends to deform along the roundness in the anteroposterior direction and the roundness in the width direction, the absorbent article fits a skin surface and becomes difficult to generate twists or leakage.

Furthermore, when the absorbent article deforms along the roundness in the width direction of the body, a vertical wrinkle tends to occur along the longitudinal direction at the central part in the width direction. However, in the absorbent article according to the present invention, since the high compression parts are concentrated at the central part of the outside curve, the vertical wrinkle may be suppressed from occurring and wearing feeling may be kept excellent.

Furthermore, since a plurality of the high compression parts are discretely arranged respectively along the inside curve and outside curve, extraneous feeling in wearing of a part hardened by the high compression part may be alleviated, and since, in addition to that the absorbent article deforms along the roundness in the anteroposterior direction of the body, a gap is provided between the high compression parts, the absorbent article tends to deform along the roundness in the width direction of the body.

As a present invention according to claim 2, the absorbent article described in claim 1 that has the low compression part of which planar shape forms a crescent shape is provided.

Since a planar shape of the low compression part is formed in a crescent shape in the invention of the claim 2, due to the low compression part, the rigidity of the central part in the width direction is formed high, and the rigidity of both side parts in the width direction is formed low. Therefore, the absorbent article tends to deform along the roundness in the width direction of the body.

As a present invention according to Claim 3, the absorbent article according to any one of claims 1 and 2 in which, among the high compression parts formed along the outside curve, the high compression part placed at the center in the width direction of the absorbent article has a maximum area among the high compression parts is provided.

According to an invention of the claim 3, since among the high compression parts formed along the outside, the high compression part arranged at the center in the width direction of the absorbent article is formed so as to have a maximum area, with the high compression part of the maximum area as a base point, both side parts tend to deform along the roundness in the width direction of the body.

As a present invention according to Claim 4, the absorbent article according to any one of claims 1 to 3 in which the high compression parts formed along the outside curve contain ones that have a planar shape long in one direction and in which a long axis direction is arranged inclined diagonally relative to a longitudinal direction line of the absorbent article is provided.

According to an invention of the claim 4, as the high compression parts formed along the outside curve, one that has a planar shape long in one direction and in which the long axis direction is arranged inclined diagonally relative to the longitudinal direction line of the absorbent article is contained. When the long axis direction of the high compression part is made not to coincide with the width direction of the absorbent article, the high compression part prevents from being disturbed to curve along the width direction of the body, and when the long axis direction of the high compression part is made not to coincide with the longitudinal direction of the absorbent article, the vertical wrinkle is prevented from occurring in the absorbent article with the high compression part as a base point.

As a present invention according to claim 5, the absorbent article according to any one of claims 1 to 4 in which among the high compression parts formed along the inside curve, the high compression part arranged at a position corresponding to a part having a large gap of adjacent high compression parts formed along the outside curve is formed with a relatively large area in accordance with its clearance.

In the invention according to the claim 5, among the high compression parts formed along the inside curve, the high compression part arranged at a position corresponding to a part having a large clearance between adjacent high compression parts formed along the outside curve is preferably formed relatively large in accordance with the clearance, thereby the rigidity due to the high compression parts formed along the inside curve and the rigidity due to the high compression parts formed along the outside curve in the low compression part complement each other to be able to prevent unnecessary wrinkle from occurring.

As a present invention according to claim 6, the absorbent article according to any one of claims 1 to 5 in which when spaced on a back end side of the absorbent article than the low compression part, a right and left pair of longitudinal direction compressed grooves are formed along in the longitudinal direction respectively on both side parts, and front end parts of the longitudinal direction compressed groove are arranged on an extension line of both ends of the low compression part is provided.

In the invention according to claim 6, when spaced on a back end side of the absorbent article than the low compression part, a right and left pair of longitudinal direction compressed grooves are formed along the longitudinal direction respectively on both side parts, front end parts of the longitudinal direction compressed groove are located on an extension line of both ends of the low compression part. Thus, the vertical wrinkle that tends to occur when the longitudinal direction compressed groove is not present on the extension line of both ends of the low compression part may be prevented and the absorbent article tends to curve along the inside curve.

As a present invention according to claim 7, the absorbent article according to any one of claims 1 to 6 in which a sum total of areas of the high compression parts formed along the inside curve and a sum total of areas of the high compression parts formed along the outside curve are substantially the same is provided.

In the invention according to claim 7, when the high compression parts formed along the inside curve and the high compression parts formed along the outside curve are formed with substantially the same sum total area, since the rigidity is not different but substantially the same between the inside curve and outside curve, the low compression part tends to fit the roundness of the body.

As a present invention according to claim 8, the absorbent article according to any one of claims 1 to 7 in which on a skin-contact surface on a back side of the absorbent article, in a plan view, a concave back low compression part is formed by denting, from a skin-contact surface side, a closed region part partitioned by a back inside curve formed of a curved line swelling on a back end side of the absorbent article, and a back outside curve that is located on a back end side than the back inside curve and made of a curved line swelling on a back end side of the absorbent article and has both ends to which both ends of the back inside curve are respectively connected is formed; and a plurality of back high compression parts is discretely formed respectively along the back inside curve and back outside curve in the back low compression part;

wherein the back high compression parts formed along the back inside curve are arranged over an entire length of the back inside curve; and the back high compression parts formed along the back outside curve are arranged at a center part of the back outside curve and are not arranged at both end parts of the back outside curve is provided.

According to the invention of the claim 8, by providing the low compression parts similarly on a back side of the absorbent article, a back part is made easy to deform along the roundness of the body to prevent the twists or leakage of the back part.

Effect of the Invention

As was detailed in the above, according to the present invention, an absorbent article that may be readily deformed along a shape of a body and is difficult to generate twists or leakage may be provided.

BRIEF DESCRIPTION OF THE DRAWINGS

FIG. 1 is a partially broken development view of a sanitary napkin 1 according to the present invention.

FIG. 2 is an arrow view taken along a II-II line of FIG. 1.

FIG. 3 is an arrow view taken along a line of FIG. 1.

FIG. 4 is an enlarged perspective view of a low compression part 10.

FIG. 5 is a front side perspective view of a groin part of a human body.

FIG. 6 is a perspective view of a sanitary napkin 1 showing a deformation state in wearing.

FIG. 7 is an enlarged plan view of a compressed groove that is not contained in the present invention.

FIG. 8 is a development view of a sanitary napkin 1 according to another embodiment.

MODES FOR CARRYING OUT THE INVENTION

In what follows, an embodiment of the present invention will be detailed with reference to the drawings.

Fundamental Structure of Sanitary Napkin 1

A sanitary napkin 1 according to the present invention includes, as shown in FIGS. 1 to 3, an impermeable back-surface sheet 2 made of a polyethylene sheet or the like, a permeable front-surface sheet 3 that rapidly passes mensural blood or vaginal discharge (hereinafter, referred to as body liquid as a whole), an absorber 4 made of cotton pulp or synthetic pulp interposed between these both sheets 2, 3, and a side nonwoven fabric 7 provided over a substantially entire length along the longitudinal direction of both end parts on a skin-contact surface side, and in the surrounding of the absorber 4, outer peripheral parts of the impermeable back-surface sheet 2 and permeable front-surface sheet 3 are connected by joining means such as an adhesive such as hot melt, heat seal, or ultrasonic seal at upper and lower end edge parts thereof, further, the impermeable back-surface sheet 2 and the side nonwoven fabric 7 extending on a lateral side than the absorber 4 are connected by joining means such as an adhesive such as a hot melt, heat seal or ultrasonic seal at both side edge parts, thus, a flap part in which the absorber is not interposed is formed. By the way, in an illustrated example, in order to improve shape retention and diffusibility of the absorber 4, the absorber 4 is surrounded by a wrapping sheet 5 made of crepe sheet or nonwoven fabric, however, the wrapping sheet 5 may not be provided. Furthermore, though not shown in the drawing, adjacent on a non-skin side of the permeable front-surface sheet 3, a second sheet made of a hydrophilic nonwoven fabric of substantially the same shape with the permeable front-surface sheet 3 may be provided.

In what follows, when a structure of the sanitary napkin 1 is described in more detail, although, as the impermeable back-surface sheet 2, a sheet material that has at least a water blocking property such as polyethylene is used, one having moisture permeability is desirably used from the viewpoint of stuffiness prevention property. As the water-blocking/moisture permeable sheet material, a micro-porous sheet obtained in such a manner that an inorganic filler is molten and kneaded in an olefin-based resin such as polyethylene or polypropylene, followed by molding into a sheet, further followed by stretching in a uniaxial or biaxial direction is preferably used. On a non-skin-contact surface (external surface) of the impermeable back-surface sheet 2, along the longitudinal direction of the napkin, one or a plurality of stripes of adhesive layers (not shown in the drawing) are formed so as to fix the sanitary napkin 1 on an underwear in wearing on the body. As the impermeable back-surface sheet 2, a polylaminated nonwoven fabric obtained by laminating a plastic film and a non-woven fabric may be used.

Then, as the permeable front-surface sheet 3, a perforated or non-perforated nonwoven fabric or a porous plastic sheet may be preferably used. As a raw-material fiber that constitutes the non-woven fabric, other than synthetic fibers such as olefin-based fibers such as polyethylene or polypropylene fibers, polyester-based fibers or polyamide-based fibers, recycled fibers such as rayon or cupra, or natural fibers such as cotton may be used, and nonwoven fabrics obtained according to an appropriate processing method such as a spunlace method, a spunbond method, a thermal bond method, a melt blown method, or a needle punch method may be used. Among these processing methods, the spunlace method is excellent in the point of having rich flexibility and draping property, and the thermal bond method is excellent in the point of having bulkiness and high compression restorability. When many permeable pores are formed in the permeable front-surface sheet 3, the body liquid is speedily absorbed to result in being excellent in dry touch property. Although the fiber of the nonwoven fabric may be any of a long fiber or a short fiber, in order to show the drape of towel cloth, the short fiber is preferably used. Furthermore, in order to make an emboss treatment easy, the olefin-based fiber such as polyethylene or polypropylene having relatively low melting point is preferably used. Still furthermore, a composite fiber of a core-sheath type fiber having a high melting point fiber as a core and a low melting point fiber as a sheath, a side-by-side type fiber, or a split type fiber may be also preferably used.

The absorber 4 interposed between the impermeable back-surface sheet 2 and the permeable front-surface sheet 3 is constituted of, for example, cotton-like pulp and an absorbent polymer. The absorbent polymer is mixed in the pulp that constitutes the absorber as, for example, particulate powder. As the pulp, chemical pulp obtained from the timber, cellulose fibers such as molten pulp, and artificial cellulose fibers such as rayon, acetate can be used, and the softwood pulp having a fiber length longer than that of the hardwood pulp is preferably used from the viewpoint of function and price.

Furthermore, the absorber 4 may be mixed with the synthetic fiber. As the synthetic fiber, for example, olefin-based synthetic fibers such as polyethylene or polypropylene, polyester-based synthetic fibers such as polyethylene terephthalate or polybutylene terephthalate, amide-based synthetic fibers such as nylon, and copolymers of these may be used, or ones obtained by mixing two kinds of these may be used. Still furthermore, a composite fiber such as a core-sheath type fiber having a high melting point fiber as a core and a low melting point fiber as a sheath, a side-by-side type fiber, or a split-type fiber may be also used. When the synthetic fiber is a hydrophobic fiber, one that is surface-treated with a hydrophilic agent is desirably used to impart the hydrophilicity to the body liquid.

As shown in FIG. 1 and FIG. 2, it is preferable to provide a center high part 6 of the absorber of which thickness is increased on a skin side in a region containing a site corresponding to a body liquid excretion part H of the absorber 4. The center high part 6 is arranged adjacent to a skin side surface of the absorber 4 and at a central part in the width direction of the absorber 4, and is formed with a width dimension and a longitudinal dimension smaller than those of the absorber 4. When a thickness of the center high part 6 is too thick, the rigidity increases to degrade the adhesiveness to the body, and when the thickness is too thin, the adhesiveness with the body liquid excretion part H is degraded. Therefore, the thickness is set to 3 to 25 mm, and preferably to 5 to 18 mm.

The center high part 6 is arranged in a region that contains a site corresponding to at least the body liquid excretion part H of a wearer. The center high part 6 may be formed into a slender shape continuing over from a region containing a site corresponding to a body liquid excretion part H to a region containing a site corresponding to a hip part groove, or may be arranged only in a region containing a site corresponding to the body liquid excretion part H and may not be arranged in a region containing a site corresponding to a hip part groove on a back side than this.

When the center high part 6 is formed into a slender shape continuing over from a region containing a site corresponding to the body liquid excretion part H to a region containing a site corresponding to a hip part groove, on a back side of the site corresponding to the body liquid excretion part H, a narrow width part in which contour lines on both sides are formed by swelling on the inside in the width direction is preferably provided. By providing the narrow width part, the absorbent article tends to fit also to fine irregularities formed on a skin surface over from a back end of the body liquid excretion part H to a start position of the hip groove to be able to improve the adhesiveness with the skin surface.

The center high part 6 contains at least the pulp fiber and synthetic fiber, and ones obtained by mixing in terms of weight at a ratio of the pulp fiber:synthetic fiber of 80 to 20:20 to 80, and preferably of 40 to 60:60 to 40 are desirable. Furthermore, the center high part 6 may contain an absorbent polymer. As the absorbent polymer, for example, cross-linked polyacrylates, self-crosslinked polyacrylates, saponified products of acrylic acid ester-vinyl acetate copolymer crosslinked products, isobutylene/maleic anhydride copolymer crosslinked products, crosslinked polysulfonates, and ones obtained by partially crosslinking water-swelling polymers such as polyethylene oxide or polyacrylamide are given. Among these, ones based on acrylic acid or acrylate having excellent amount of water absorption and water absorption speed are preferable. A water-absorbing power and absorption speed may be adjusted by adjusting a cross-linking density and a crosslinking density gradient in the production process of the absorbent polymer having water absorption performance. When a blending amount is increased from the necessity of promoting permeation of the center high part 6 to the absorber 4 side, a so-called gel blocking phenomenon occurs. Therefore, the absorbent polymer is desirably blended at a ratio of 1 to 10% in terms of weight relative to a total weight of the pulp fiber and synthetic fiber. By the way, when the content of the absorbent polymer exceeds 50%, tangling between pulp fibers becomes deficient to tend to undesirably cause degradation of the sheet strength to result in causing breakage or crack.

A width dimension of the permeable front-surface sheet 3 is set to, in an illustrated example, as shown in cross-section diagrams of FIG. 2 and FIG. 3, a slightly longer than a width of the absorber 4 to cover only the absorber 4, and, outside thereof, a side nonwoven fabric 7 separate from the permeable front-surface sheet 3, a side nonwoven fabric 7 that specifically prevents permeation of menstrual blood or vaginal discharge, or in accordance with an object of enhancing skin contact feeling, a side nonwoven fabric 7 constituted with appropriately water-repellent treated or hydrophilic treated nonwoven fabric raw material is provided. As such side nonwoven fabric 7, ones formed according to an appropriate processing method with natural fibers, synthetic fibers or recycled fibers as a raw material may be used. However, in order to make free from stiff feeling and to prevent the stuffiness, a nonwoven fabric of which basis weight is suppressed to impart air permeability is preferably used. Specifically, a nonwoven fabric that is produced with a basis weight controlled to 13 to 23 g/m² is desirably used, and, in order to secure prevention of permeation of the body liquid, water-repellent treated nonwoven fabrics coated with silicone-based, paraffin-based, or alkyl chromic chloride-based water repellent agent may be preferably used.

In the side nonwoven fabric 7, as shown in FIG. 2 and FIG. 3, an outside part than an intermediate part in the width direction is adhered with an adhesive such as hot-melt over a range from a predetermined inside position to an outer edge of the non-permeable back-surface sheet 2, from the side nonwoven fabric 7, the impermeable buck-surface sheet 2 and the laminate sheet part, a flap part where the absorber 4 is not interposed on both side parts of the absorber 4 is formed. In the flap part, a left and right pair of wing-like flaps W, W are formed at a position of absorber side part substantially corresponding to the body liquid excretion part H, and at a position on a hip part side than this (back side), hip-hold flaps $W_B$, $W_B$ may be formed. On each of outer surface sides of these wing-like flaps W, W and hip-hold flaps $W_B$, $W_B$, an adhesive layer (not shown in the drawing) is provided, and, in wearing shorts, the wing-like flaps W, W are folded back on the opposite side at a folding line RL position of a basis end part, is wound to a crotch part of the short to fasten and the hip-hold flaps $W_B$, $W_B$ are fastened to an inner surface of the short.

On the other hand, an inner side part of the side nonwoven fabric 7 is folded into substantially two folds, and in the inside of the two-folded sheet, one or a plurality of, in the illustrated example, three thread-like elastic stretchable members 9, 9 . . . of which both ends or appropriate positions in the longitudinal direction are fixed to an intermediate part in the height direction are provided in a state where both ends or an appropriate position in the longitudinal direction are fixed. The double-folded sheet part is, in the anteroposterior edge parts, as shown in FIG. 3, adhered to the absorber 4 side in a state once folded on the outside, thus, as shown in FIG. 2, linear solid gathers BS, BS rising on the front side while inclining toward the outside are formed in a left and right pair.

Compression Part

In the present sanitary napkin 1, on a skin-contact on a front side of the sanitary napkin 1, a concave low compression part 10 dented from an outside surface side of the permeable front sheet 3 is formed. The low compression part 10 is, as shown in detail in FIG. 4, in a plan view, formed by denting, from a skin-contact surface side (an outer surface side of the permeable front-surface sheet) toward a non-skin side (impermeable back-surface sheet 2 side), a closed region part partitioned by an inside curve 12 formed of a curved line swelling on a front end side of a sanitary napkin 1 and an outside curve 13 that is located on the front end side of the sanitary napkin 1 than the inside curve 12 and formed of a curved line swelling on the front end side of the sanitary napkin 1, and has both ends that are connected respectively to both ends of the inside curve 12. In the low compression part 10, a plurality high compression parts 11, 11 . . . are formed discretely respectively along the inside curve 12 and outside curve 13. The high compression parts 11 . . . (14 . . . ) formed along the inside curve 12 are arranged over an entire length of the inside curve 12, and the high compression parts 11 . . . (15 . . . ) formed along the outside curve 13 are arranged at a center part of the outside curve 13 and are not arranged at both end parts of the outside curve 13.

The low compression part 10 is partitioned by the inside curve 12 and outside curve 13 to form a crescent shape that has a planar shape along the substantially width direction of the sanitary napkin 1 and a central part that swells on a front end side of the sanitary napkin 1. That is, the low compression part 10 is formed bilaterally symmetrically with respect to a central line CL in the longitudinal direction of the sanitary napkin 1 and is formed such that on the central line CL in the longitudinal direction, a part where the clearance in the longitudinal direction of napkin of the inside curve 12 and outside curve 13 becomes a maximum is located, and, as goes toward both side parts of the sanitary napkin 1, the clearance becomes gradually smaller.

A dimension B in the napkin width direction of the low compression part 10 is formed smaller than the clearance between the side nonwoven fabrics 7, 7 on both sides and at 40 to 80%, preferably 50 to 70% relative to the width of the absorber. When the width dimension B is smaller than 40% relative to the width of the absorber, when the absorber 4 is deformed, the low compression part 10 is difficult to work as the base point, and when the width dimension B exceeds 80% of the width of the absorber, the absorber 4 becomes too hard due to the low compression part 10 to result in generating extraneous feeling in wearing.

Furthermore, a dimension L in the longitudinal direction of the sanitary napkin on a centerline CL in the longitudinal direction of the sanitary napkin 1 is set to 5 to 20 mm, and desirably to 10 to 15 mm. When the longitudinal dimension L is smaller than 5 mm, the effect of enhancing the rigidity due to the low compression part 10 is difficult to obtain, and when the longitudinal dimension L exceeds 20 mm, the absorber 4 becomes too hard to result in feeling extraneous feeling in wearing.

The low compression part 10 is formed between a front end side than a site corresponding to the body liquid excretion part H of a wearer, specifically a front end side than a front end of the center high part 6, and more specifically a front end side than the wing-like flap W formed at both side parts, and a front end of the absorber 4. Thus, the sanitary napkin 1 may deform along the roundness of a front part of a body on a front end side than a groin part of the wearer.

A clearance Y between the low compression part 10 and a front end of the absorber 4 is set to 5 to 30 mm, and preferably to 10 to 20 mm. When the clearance Y is smaller than 5 mm, the effect of deforming a front end part of the absorber 4 with the low compression part 10 as the base point is difficult to obtain, and when the clearance Y exceeds 30 mm, the wrinkle or twists tend to occur on a front end side than the low compression part 10.

The high compression parts 11, 11 . . . are dot-like compression parts formed within the low compression part 10 partitioned by the inside curve 12 and outside curve 13 and formed with a compression depth deeper than that of the low compression part 10. The high compression parts 11 . . . are arranged respectively along the inside curve 12 and outside curve 13. That the high compression part 11 is arranged along the inside curve 12 or outside curve 13 means whether a periphery of the high compression part 11 is arranged so as to contact with the inside curve 12 or outside curve 13, or if not contact with the respective curves 12, 13, is arranged on the respective curved line sides, with the center line drawn along a center of the clearance part of the inside curve 12 and the outside curve 13 of the low compression part 10 as a boundary. However, among the high compression parts 14 . . . formed along the inside curve 12, high compression parts 14a arranged at both end parts of the inside curve 12, due to a shorter clearance with the outside curve 13, may exude on the outside curve 13 side than the central line of the low compression part 10. However, even in this case, one arranged so as to contact with the inside curve 12 are the high compression parts 11 formed along the inside curve 12.

The low compression part 10 is, as shown in FIG. 4, partitioned into: a high compression part arrangement region 16 on the inside in which a plurality of high compression parts 14, 14 . . . are discretely arranged over a substantially entire length of the inside curve 12; a high compression part arrangement region 17 on the outside in which a plurality of high compression parts 15, 15 . . . are discretely arranged concentrated at a center part of the outside curve 13; and a high compression part absent region 18 where in each of both sides of the outside curve 13, a high compression part is not arranged.

In the high compression part arrangement region 16 on the inside, it is better that the clearances along the inside curve 12 of the adjacent high compression parts 14, 14 are set to substantially the same, or a ratio of the smallest clearance and the largest clearance is set to three times or smaller, preferably 2.5 times or smaller. Thus, the rigidity due to the high compression parts 14 . . . may be intensified substantially uniformly over a substantially entire length of the inside curve 12.

The number of the high compression parts 14 . . . formed along the inside curve 12 is set to 4 to 20, preferably to 6 to 14. As shown in FIG. 4, it is preferable that the high compression parts 14 formed along the inside curve 12 are not arranged on the central line CL in the longitudinal direction of the sanitary napkin 1 but are arranged bilaterally symmetrically on both sides of the central line CL.

On the other hand, a length along the outside curve 13 of the high compression part arrangement region 17 is set to 30 to 70% of an entire length of the outside curve 13, and preferably to 40 to 60%. When the length of the high compression part arrangement region 17 is smaller than 30% of an entire length of the outside curve 13, a sufficient enhancement effect due to the high compression parts 15 is not desired, and when the length exceeds 70% of the entire length of the outer curve 13, the high compression part absent region 18 of the both side parts becomes too small to be difficult to generate deformation of front both side parts of the sanitary napkin 1.

The number of the high compression parts 15 arranged in the high compression part arrangement region 17 is set to 3 to 15, and preferably to 3 to 7. In the high compression part arrangement region 17, a pattern in which the high compression parts 15 are arranged on the central line CL in the longitudinal direction of the sanitary napkin 1, and one or a plurality of high compression parts 15 are bilaterally symmetrically arranged on both sides thereof is preferred. When the high compression parts 15 are arranged on the central line CL in the longitudinal direction, with the central high compression parts 15 as a base point, both sides tend to curve in the width direction to result in fitting to a shape of the body.

The high compression parts 14 formed along the inside curve 12, and the high compression parts 15 formed along the outside curve 13 are preferably arranged to a maximum extent in zigzags at positions that are not overlapped in radial directions of the inside curve 12 and outside curve 13. Thereby, when these high compression parts 14, 15 are arranged at positions that overlap in the radial direction, the generation of the vertical wrinkle or the like may be prevented. By the way, the high compression parts 14 and 15 may overlap partially in the radial direction or may generate a slight gap.

Since in the sanitary napkin 1 formed with the above constitution, as shown in FIG. 5 and FIG. 6, the inside curve 12 is enhanced in the rigidity over an entire length due to the high compression parts 14 formed along the inside curve 12, and the center part of the outside curve 13 is enhanced in the rigidity by the high compression parts 15 formed along the outside curve 13, with these curved parts of which rigidity is heightened as a base point, the sanitary napkin 1 tends to curve in the longitudinal direction, and due to rise-up of the front side along the inside curve 12, tends to deform along the roundness in the anteroposterior direction of the body. Furthermore, since a high compression part absent region 18 in which the high compression part 15 is not arranged is provided to both end parts of the outside curve 13, the rigidity degrades relatively to the high compression part arrangement region 17 of the central part, both side parts on the front side than the low compression part 10 of the sanitary napkin 1 tends to curve on a skin side and tends to deform along the roundness in the width direction of the body. Thus, since the front side of the sanitary napkin 1 tends to deform along the roundness in the anteroposterior direction and the roundness in the width direction, the sanitary napkin 1 fits to a skin surface to be difficult to generate twists or leakage.

Furthermore, when the sanitary napkin 1 is deformed along the roundness in the width direction of the body, the vertical wrinkle tends to occur along the longitudinal direction at the center part in the width direction. However, since the high compression part arrangement region 17 is provided at the center part of the outside curve 13, the center part in the width direction is reinforced by the high compression part 15 of the high compression part arrangement region 17, may suppress occurrence of the vertical wrinkle and may maintain the wearing feeling excellent.

Furthermore, since the high compression parts 11 are discretely arranged respectively along the inside curve 12 and outside curve 13, extraneous feeling in wearing due to enhanced rigidity by the high compression part 11 may be alleviated, and the sanitary napkin 1 tends to be deformed along the roundness in the anteroposterior direction of the body, in addition thereto, tends to be deformed along the roundness in the width of the body.

As shown in FIG. 4, among the high compression parts 15 . . . formed along the outside curve 13, the high compression part 15a arranged on the center line CL in the longitudinal direction of the sanitary napkin 1 preferably has a maximum area among all high compression parts 11 . . . formed within the low compression part 10. Thus, both side parts tend to deform along the roundness of the body with the high compression part 15a of the maximum area as a base point. An area of the high compression part 15a of the maximum area is preferably set to about 5 times to 10 times an area of the smallest high compression part 11.

Furthermore, the high compression part 15a of the maximum area is preferably formed, as shown in FIG. 4, in a planar shape having a plurality of convex parts projected toward outside (a star shape in the illustrated drawing) such as a polygonal shape, a star shape or a flower shape, and when the high compression part 15a at this time is arranged such that the convex part contacts with a center of the outside curve 13, both side parts from the center part in the width direction preferably tends to be curved and deformed with a convex part in contact with the outside curve 13 of the high compression part 15a of the maximum area as a base point.

As shown in FIG. 4, it is preferable that the high compression parts 15 formed along the outside curve 13 have a planar shape long in one direction and contain a high compression part 15b in which a long axis direction is arranged inclined diagonally relative to a longitudinal direction line (a central line CL in the longitudinal direction) of the sanitary napkin 1. The high compression parts 15b are preferably arranged respectively on both sides of the high compression part 15a of the maximum area arranged at the center part in the width direction. When the long axis direction of the high compression part 15b is not coincided with the width direction of the sanitary napkin 1, a curving deformation along the width direction of a part in which the high compression part 15b is arranged is not disturbed, and when the long axis direction of the high compression part is not coincided with the longitudinal direction of the sanitary napkin 1, the vertical wrinkle with the high compression part 15b as a base point may be prevented from occurring.

The high compression part 15b is preferably arranged, as in the illustrated example, such that an inside in the width direction inclines toward a center side of the sanitary napkin 1. At this time, an angle α formed between the long axis of the high compression part 15b and the center line CL in the longitudinal direction of the sanitary napkin 1 is set to 30 to 60°, in particular, preferably to 40 to 50°. When the high compression part 15b thus arranged is provided on both sides of the center in the width direction, the low compression part 10 region tends to further curve along the width direction with the high compression part 15b as a base point.

A planar shape of the high compression part 15b may be any one of ones having a planar shape longer in one direction such as a drip shape, a long circle, an ellipse, or a rectangular shape. However, as in the illustrated example, a drip shape in which one side in the longitudinal direction is formed with a width wider than the other side is preferable. At this time, as in the illustrated example, when one side formed with a larger width is arranged toward a side nearer to the outside curve 13 (the front end side of the sanitary napkin 1), the force tends to work on the outside curve 13 side, and the sanitary napkin 1 tends to curve along the outside curve 13.

On the other hand, the high compression parts 14 . . . formed along the inside curve 12 may be formed with substantially the same area over an entire length, or, as shown in FIG. 4, may be formed with a partially relatively large area. Specifically, as was described above, the high compression parts 14 formed along the inside curve 12 are arranged at positions that do not overlap with the high compression parts 15 formed along the outside curve 13 in radial directions of the inside curve 12 and outside curve 13, and arranged substantially coinciding with the clearance part of the adjacent high compression parts 15, 15 formed along the outside curve 13, however, among the high compression parts 14 . . . formed along the inside curve 12, the high compression part 14*b* arranged at a position corresponding to a part having a large clearance of the adjacent high compression parts 15, 15 formed along the outside curve 13 may be formed with a relatively large area in accordance with the clearance. Thus, since with respect to radial directions of the inside curve 12 and outside curve 13, a part in which the rigidity is remarkably degraded due to absence of the high compression parts 14, 15 is not formed, the rigidity due to the high compression parts 14 . . . formed along the inside curve 12 within the low compression part 10 and the rigidity due to the high compression parts 15 . . . formed along the outside curve 13 complement each other to be able to prevent occurrence of unnecessary wrinkle.

In the sanitary napkin 1, as shown in FIG. 1, other than the low compression part 10 formed on a front side, at a position of a proximity outside part of the center high part 6, compressed grooves dented from an outer surface side of the permeable front-surface sheet 3 toward the impermeable back-surface sheet 2 may be formed. In an example specifically shown in FIG. 1, the compressed grooves are constituted of: front side longitudinal direction compressed grooves 20, 20 that are arranged spaced on a back end side of the sanitary napkin 1 than the low compression part 10 and continuously formed along the substantially longitudinal direction of the napkin 1 respectively on both side parts over from a region containing a site corresponding to the body liquid excretion part H to a region containing a site corresponding to a hip part groove; back side longitudinal direction compressed grooves 21, 21 that are arranged spaced on a back side of the front side longitudinal direction compressed groove 20, and are continuously formed along the substantially longitudinal direction of the napkin 1 respectively on both side parts of a site corresponding to a back end part of a hip part groove; and a back end curve-shaped compressed groove 22 that is arranged spaced on a back side of the back side longitudinal direction compressed grooves 21, 21, crosses the longitudinal direction center line CL of the napkin 1 in the width direction, and is formed of a curved shape swelling toward a back direction. These compressed grooves 20 to 22 are obtained by compressing integrally over from the permeable front-surface sheet 3 to the absorber 4 by hot embossing from an outer surface side of the permeable front-surface sheet 3.

The front longitudinal direction compressed grooves 20, 20 arranged adjacent on a back side of the low compression part 10 are, as shown in FIG. 4, desirably arranged such that a front end part is located on an extension line S of both ends of the low compression part 10. When a front end part of the front longitudinal direction compressed groove 20 is arranged on the extension line S like this, wrinkles occurring along the extension line S when the low compression part 10 is deformed along the roundness of the body may be suppressed. By contrast, as shown in FIG. 7, when the front end part of the front longitudinal direction compressed groove 20 is not present on the extension line S of both ends of the low compression part 10, in the illustrated example, when the front end part of the front longitudinal direction compressed groove 20 is arranged on an inner side than the extension line S of both ends of the low compression part 10, the wrinkles of the low compression parts 10 deformed along the roundness of the body tend to occur along the extension line S. Furthermore, when the wrinkle occurs along the extension line S, the low compression part 10 becomes difficult to deform. Here, the extension line S of both ends of the low compression part 10 is a tangent line at both ends of the low compression part 10 of the center line going through a center of a spaced part between the inside curve 12 and outside curve 13 of the low compression part 10. Furthermore, that a front end part of the front longitudinal direction compressed groove 20 is located on the extension line S means that the extension line S goes through within the groove width of the front end part of the front longitudinal direction compressed groove 20.

Next, a sum total of areas of the high compression parts 14 . . . formed along the inside curve 12 and a sum total of areas of the high compression parts 15 . . . formed along the outside curve 13 are preferably set to substantial the same. That these areas are substantially the same is that an area of one side is within ±5%, and preferably within ±3% of the other area side. Thus, since the rigidity enhanced by the high compression parts 14, 15 becomes substantially the same between the inside curve 12 and outside curve, the low compression part 10 tends to deform along the roundness of the body to result in improving the fitting property.

Another Embodiment

In the above embodiment, the low compression part 10 is provided only on a front side of the sanitary napkin 1 and on a back side, the back end curve-shaped compressed groove 22 with constant groove width formed of a curved shape swelling toward aback direction is arranged. However, as shown in FIG. 8, in place of the back end curve-shaped compressed groove 22 (illustrated example), or spaced in a back direction of the back end curve-shaped compressed groove 22, in a plan view, a concave back low compression part 30 obtained by denting, from a skin-contact surface side, a closed region part partitioned by a back inside curve 32 formed of a curved line swelling on a back end side of a sanitary napkin 1, and a back outside curve 33 that is located on a back end side than the back inside curve 32, formed of a curved line swelling on a back end side of the sanitary napkin 1, and has both ends that are respectively connected the both ends of the back inside curve 32 is formed; and, in the back low compression part 30, a plurality of back high compression parts 31 are discretely formed respectively along the back inside curve 32 and back outside curve 33, wherein the back high compression parts 34 formed along the back inside curve 32 are arranged over an entire length of the back inside curve 32, and the back high compression parts 35 formed along the back outside curve 33 are arranged at a center part of the back outside curve 33 and are not arranged at both end parts of the back outside curve 33. Thus, similarly also on a back side of the sanitary napkin 1, the sanitary napkin tends to deform along the roundness in the anteroposterior direction of the body and along the roundness in the width direction and the twists or leakage becomes difficult to occur.

EXPLANATION OF MARKS

1 . . . SANITARY NAPKIN
2 . . . IMPERMEABLE BACK-SURFACE SHEET
3 . . . PERMEABLE FRONT-SURFACE SHEET
4 . . . ABSORBER
5 . . . WRAPPING SHEET
6 . . . CENTER HIGH PART
7 . . . SIDE NONWOVEN FABRIC

9 ... THREAD-LIKE ELASTIC STRETCHABLE MEMBER
10 ... LOW COMPRESSION PART
11/14/15 ... HIGH COMPRESSION PART
12 ... INSIDE CURVE
13 ... OUTSIDE CURVE
16/17 ... HIGH COMPRESSION PART ARRANGEMENT REGION
18 ... HIGH COMPRESSION PART ABSENT REGION
20 ... FRONT LONGITUDINAL DIRECTION COMPRESSED GROOVE
21 ... BACK LONGITUDINAL DIRECTION COMPRESSED GROOVE
22 ... BACK END CURVE-SHAPED COMPRESSION GROOVE

The invention claimed is:

1. An absorbent article comprising:
an absorber interposed between a permeable front-surface sheet and an impermeable back-surface sheet,
wherein on a skin-contact surface on a front side of the absorbent article, in a plan view, a concave low compression part obtained by denting, from a skin-contact surface side, a closed region part partitioned by an inside curve formed of a curved line swelling on a front end side of the absorbent article, and an outside curve that is located on a front end side than the inside curve, is formed of a curved line swelling on a front end side of the absorbent article, and has both ends to which both ends of the inside curve are respectively connected is formed; and,
in the low compression part, a plurality of high compression parts is discretely formed respectively along the inside curve and outside curve,
wherein the high compression parts formed along the inside curve are arranged over an entire length of the inside curve, and the high compression parts formed along the outside curve are arranged at a center part of the outside curve and are not arranged at both end parts of the outside curve.

2. The absorbent article according to claim 1, wherein low compression part has a planar shape formed into crescent shape.

3. The absorbent article according to claim 1, wherein, among the high compression parts formed along the outside curve, a high compression part placed at the center in the width direction of the absorbent article has a maximum area among the high compression parts.

4. The absorbent article according to claim 1, wherein the high compression parts formed along the outside curve contain one that has a planar shape long in one direction and is arranged such that a long axis direction is inclined diagonally relative to a longitudinal direction line of the absorbent article.

5. The absorbent article according to claim 1, wherein among the high compression parts formed along the inside curve, a high compression part arranged at a position corresponding to a part having a large clearance of adjacent high compression parts formed along the outside curve is formed with a relatively large area in accordance with the clearance.

6. The absorbent article according to claim 1, wherein when spaced on a back end side of the absorbent article than the low compression part, a right and left pair of longitudinal direction compressed grooves are formed along in the longitudinal direction respectively on both side parts, and front end parts of the longitudinal direction compressed grooves are located on an extension line of both ends of the low compression part.

7. The absorbent article according to claim 1, wherein a sum total of areas of the high compression parts formed along the inside curve and a sum total of areas of the high compression parts formed along the outside curve are substantially the same.

8. The absorbent article according claim 1, wherein on a skin-contact surface on a back side of the absorbent article, in a plan view, a concave back low compression part is formed by denting, from a skin-contact surface side, a closed region part partitioned by a back inside curve formed of a curved line swelling on a back end side of the absorbent article, and a back outside curve that is located on a back end side than the back inside curve and made of a curved line swelling on a back end side of the absorbent article and has both ends that are connected respectively to both ends of the back inside curve is formed; and
a plurality of back high compression parts formed discretely respectively along the back inside curve and back outside curve is formed in the back low compression part,
wherein the back high compression parts formed along the back inside curve are arranged over an entire length of the back inside curve; and
the back high compression parts formed along the back outside curve are arranged at a center part of the back outside curve and are not arranged at both end parts of the back outside curve.

* * * * *